(12) United States Patent
Osawa et al.

(10) Patent No.: US 7,754,477 B2
(45) Date of Patent: Jul. 13, 2010

(54) INCUBATOR

(75) Inventors: Shinji Osawa, Ora-gun (JP); Yasuhiro Kikuchi, Ota (JP)

(73) Assignees: Sanyo Electric Co., Ltd., Moriguchi-shi (JP); Sanyo Electric Biomedical Co., Ltd., Moriguchi-shi (JP)

( * ) Notice: Subject to any disclaimer, the term of this patent is extended or adjusted under 35 U.S.C. 154(b) by 1123 days.

(21) Appl. No.: 10/965,887

(22) Filed: Oct. 18, 2004

(65) Prior Publication Data

US 2005/0084420 A1   Apr. 21, 2005

(30) Foreign Application Priority Data

Oct. 20, 2003   (JP)   ............... 2003-359939

(51) Int. Cl.
- C12M 1/00 (2006.01)
- C12M 3/00 (2006.01)
- B01L 3/00 (2006.01)
- A21B 1/00 (2006.01)
- A21B 1/22 (2006.01)
- G05D 22/02 (2006.01)

(52) U.S. Cl. ................. 435/303.1; 435/303.2; 435/809; 422/99; 236/44 C; 219/407

(58) Field of Classification Search ............... 435/303.1, 435/303.2, 809; 422/99; 236/44 C; 219/407
See application file for complete search history.

(56) References Cited

U.S. PATENT DOCUMENTS

| | | | |
|---|---|---|---|
| 4,701,415 A * | 10/1987 | Dutton et al. ............ 435/286.6 |
| 5,519,188 A * | 5/1996 | Yuichi et al. ................. 219/407 |
| 5,783,439 A * | 7/1998 | Reichler et al. .......... 435/286.1 |
| 6,255,103 B1 * | 7/2001 | Tamaoki et al. .......... 435/303.1 |
| 6,503,751 B2 * | 1/2003 | Hugh ...................... 435/303.1 |

FOREIGN PATENT DOCUMENTS

| JP | 07-031462 | 2/1995 |
|---|---|---|
| JP | 2000-166536 | 6/2000 |

* cited by examiner

*Primary Examiner*—Walter D Griffin
*Assistant Examiner*—Lydia Edwards
(74) *Attorney, Agent, or Firm*—Kratz, Quintos & Hanson, LLP (57) ABSTRACT

An object of the invention is to provide a multigas incubator capable of shortening humidity-returning time after closing its door. The incubator comprises an adiabatic box main body having an opening on a front face thereof, an adiabatic door mounted on the adiabatic box main body in an openable and closable manner, a transparent inner door for openably closing the opening, and an incubation room surrounded by the inner door and the adiabatic box main body for incubating samples such as cells, microbes and the like. The adiabatic box main body comprises an outer box made of a metal, an inner box made of a metal, a heat insulating material arranged inside the outer box between the outer and inner boxes, and an air layer arranged more inside than the heat insulating material. Gases supplied for controlling concentrations of gases in the incubation room are jetted into humidification water.

3 Claims, 5 Drawing Sheets

INCUBATOR

BACKGROUND OF THE INVENTION

The present invention relates to a carbon dioxide gas ($CO_2$) incubator or a multigas incubator as an incubator for incubating cultures (samples) such as cells, microbes and the like.

The incubator maintains a temperature and a $CO_2$ concentration constant therein (in incubation room) and keeps its inside in a sterile condition to incubate cultures (samples) such as cells or microbes as incubation targets. Therefore, the inside of the incubator must be periodically processed by sterilization treatment. There has been a multigas incubator provided with a heater and its controller for adjusting the temperature in the incubation room (storing room), gas supply means for supplying and controlling supply gases such as $CO_2$, $O_2$ and the like for controlling concentrations of gases, and a humidifying tray for adjusting the humidity, respectively for the purpose of incubating samples in the incubation room.

On the other hand, as disclosed in Japanese Patent Application Laid Open Nos. 31,462/1995 and 166,536/2000, there have been incubating devices each comprise an outer box provided on its inner side with a heat insulating material for uniformly and effectively heating the inside of an inner box to improve its temperature-returning characteristics, the inner box arranged inside the outer box with a space more inside than the heat insulating material, and a heating device secured in the space in contact with the inner box for heating the inside thereof. The space described above serves to form an air layer (air jacket) provided for the thermal insulation between the incubation room of the incubator and its outside and promotion of heat transfer by natural convection. As shown in the latter patent literature, particularly, a humidifying tray is arranged at the bottom of the incubation room for storing humidification water for controlling the humidity in the incubation room.

On the other hand, a multigas incubator accommodates therein important and valuable cells, microbes or the like to be incubated so that variations in humidity in the incubation room cannot be avoided by the ambient air entering the incubator when an inner door is opened. Taking account of the fact that variations in humidity adversely affect samples such as cells and the like to be incubated, it is needed to shorten the time as much as possible, which is required to return a desired humidity after the inner door is once opened and then closed (that is, humidity-returning time). In the case incubating human cells for ectosomatic fertilization or animal fertile eggs as samples, particularly, these samples are likely to be remarkably affected by humidity so that extra precautions are required. In the incubators for treating such samples, the concentration of $O_2$ is frequently set and kept at approximately 5%, and dried $N_2$ gas is supplied into an incubation room after closing the door in order to control the concentration of $O_2$. Consequently, the humidity-returning time would be adversely prolonged by such a supply of the dried gas.

SUMMARY OF THE INVENTION

It is an object of the invention to provide an incubator such as a multigas incubator capable of shortening humidity-returning time after closing its inner door. In addition thereto, it is an object of the invention to improve evaporation faculty of humidification water for controlling the humidity in the incubation room.

The incubator (1) according to the invention comprises an adiabatic box main body (2) having an opening (2A) on a front face thereof, an adiabatic door (7) mounted on the adiabatic box main body (2) in an openable and closable manner, a transparent inner door (3) for openably closing the opening (2A), and an incubation room (4) surrounded by the inner door (3) and the adiabatic box main body (2) for incubating samples such as cells, microbes and the like, the adiabatic box main body (2) comprising an outer box (21) made of a metal, an inner box (22) made of a metal, a heat insulating material (24) arranged inside the outer box between the outer and inner boxes (21, 22), and an air layer (25) arranged more inside than the heat insulating material (24), and gas supplied for controlling gas concentration in the incubation room (4) is jetted into humidification water (16).

According to this invention, the gases supplied for controlling the gas concentration in the incubation room (4) are jetted into the humidification water (16) so that the supplied gases absorb moisture to be humidified, while rising in the humidification water, thereby enabling the humidified gases to be circulated in the incubation room to contribute to the improvement of humidification faculty of the humidifying tray (15) in addition to the supply of gases.

Moreover, the incubator (1) according to the present invention further comprises a humidifying tray (15) for storing humidification water (16) for controlling the humidity in the incubation room (4), and gas supply means (17) for supplying gas for controlling the gas concentration in the incubation room (4), and a gas outlet port (17A) of the gas supply means is immersed in the humidification water (16) in the humidifying tray (15).

According to this invention, as a gas outlet port (17A) of the gas supply means for supplying gases for controlling the concentrations of the gases in the incubation room (4) is immersed in the humidification water (16) in the humidifying tray (15) for controlling the humidity in the incubation room (4), the gases supplied from the gas outlet port (17A) can be jetted into the humidification water (16) in the humidifying tray, making it possible to humidify the supply gases and to circulate them into the incubation room (4).

Further, the incubator (1) according to the present invention further comprises a support (18) for supporting the gas outlet port (17A) of the gas supply means (17).

According to this invention, as there is provided the support (18) for supporting the gas outlet port (17A) of the gas supply means (17), the gas outlet port (17A) of the gas supply means can be supported by the support (18) so as to be immersed in the humidification water (16) in the humidifying tray (15).

In the incubator (1) of the present invention, moreover, the support (18) comprises restraining means (18A) for restraining rising of the gas.

According to this invention, as the support (18) comprises restraining means (18A) for restraining rising of the gases, a space can be formed between the restraining means (18A) and the water surface of the humidification water so that the evaporation of the humidification water is promoted to improve the evaporation faculty by the gases accumulated in the space.

Furthermore, the incubator (1) of the present invention comprises an adiabatic box main body (2) having an opening (2A) on a front face thereof, an adiabatic door (7) mounted on the adiabatic box main body in an openable and closable manner, a transparent inner door (3) for openably closing the opening, an incubation room (4) surrounded by the inner door and the adiabatic box main body for incubating samples such as cells, microbes and the like, a humidifying tray (15) for storing humidification water (16) for controlling the humidity in the incubation room, gas supply means (17) for supplying gas for controlling gas concentration in the incubation room, and a duct (11) and a circulation blower (14) for causing forced convection of air in the incubation room, and gas supplied for controlling the gas concentration in the incubation room (4) is jetted into the humidification water (16).

According to this invention, the incubator (1) of the present invention comprises an adiabatic box main body (2) having an opening (2A) on a front face thereof, an adiabatic door (7) mounted on the adiabatic box main body in an openable and closable manner, a transparent inner door (3) for openably closing the opening, an incubation room (4) surrounded by the inner door and the adiabatic box main body for incubating samples such as cells, microbes and the like, a humidifying tray (15) for storing a humidification water (16) for controlling the humidity in the incubation room, gas supply means (17) for supplying gases for controlling concentrations of gases in the incubation room, and a duct (11) and a circulation blower (14) for causing forced convection of air in the incubation room, and gases supplied for controlling concentrations of the gases in the incubation room (4) are jetted into the humidification water (16). Therefore, the gases supplied from the gas supply means (17) absorb moisture to be humidified, while naturally rising in the humidification water (16) in the humidifying tray (15) so that the humidified gases can be guided into the incubation room (4) by the circulation blower (14) and the duct (11), thereby promoting the evaporation of the humidification water (16) by the supplied gases to contribute to the improvement of evaporation faculty of the humidifying tray (15) in addition to the supply of gases.

In the incubator (1) of the present invention, further, a gas outlet port (17A) of the gas supply means is immersed in the humidification water (16) in the humidifying tray.

According to this invention, the gas outlet port (17A) of the gas supply means for supplying gases for controlling the concentrations of the gases in the incubation room (4) is immersed in the humidification water (16) in the humidifying tray (15) stored for controlling the humidity in the incubation room (4). Therefore, the gases ($O_2$ and $N_2$) supplied from the gas outlet port (17A) can be jetted into the humidification water (16) in the humidifying tray so that the supplied gases can be humidified and circulated into the incubation room (4).

In the incubator (1) of the present invention, further, the humidifying tray (15) is arranged in the duct (11) and at the bottom of the incubation room (4).

According to this invention, the humidifying tray (15) is arranged in the duct (11) and at the bottom of the incubation room (4) so that the humidified gases can be jetted with high efficiency into the air passage K formed by the circulation blower (14) and the duct (11) and leading to the incubation room (4).

The incubator (1) according to the present invention further comprises a support (8) for supporting the gas outlet port (17A) of the gas supply means.

According to this invention, there is provided the support (8) for supporting the gas outlet port (17A) of the gas supply means so that the gas outlet port (17A) of the gas supply means can be supported by the support (18) so as to be immersed in the humidification water (16) in the humidifying tray (15).

In the incubator (1) according to the present invention, the support (18) forms a passage in the same direction as the air flowing direction formed by the duct (11).

According to the invention, the support (18) forms a passage in the same direction as the air flowing direction formed by the duct (11) so that the humidified gases can be conducted with high efficiency in the air flowing direction formed by the circulation blower (14) and the duct (11) and leading to the incubation room (4). Also, the spacing between the support (18) and the water surface can be less than the spacing between the water surface and the duct (11) so that the air velocity in the space formed by the support (18) and the water surface is higher than the velocity of the air flow in the air passage K, thereby enabling the evaporation faculty of the humidification water to be improved by the increase in the velocity of the air flow.

The incubator (1) comprises an adiabatic box main body (2) having an opening on its front face, an adiabatic door (7) mounted on the adiabatic box main body in an openable and closable manner, a transparent inner door (3) for openably closing the opening, an incubation room (4) surrounded by the inner door (3) and the adiabatic box main body (2) for incubating samples such as cells, microbes and the like, a duct (11) and a circulation blower (14) for causing forced convection of air in the incubation room, a humidifying tray (15) arranged in the duct (11) and at the bottom of the incubation room (4) for storing humidification water (16) for controlling the humidity in the incubation room, and gas supply means (17) for supplying gas for controlling gas concentration in the incubation room, the adiabatic box main body comprising an outer box (21) made of a metal, an inner box (22) made of a metal, a heat insulating material (24) arranged inside the outer box between the outer and inner boxes, and an air layer (25) arranged more inside than the heat insulating material, and the incubator further comprises a support (18) for immersing the gas outlet port (17A) of the gas supply means (17) in the humidification water (16) in the humidifying tray (15).

According to the invention, the incubator (1) comprises an adiabatic box main body (2) having an opening on its front face, an adiabatic door (7) mounted on the adiabatic box main body in an openable and closable manner, a transparent inner door (3) for openably closing the opening, an incubation room (4) surrounded by the inner door (3) and the adiabatic box main body (2) for incubating samples such as cells, microbes and the like, a duct (11) and a circulation blower (14) for causing forced convection of air in the incubation room, a humidifying tray (15) arranged in the duct (11) and at the bottom of the incubation room (4) for storing humidification water (16) for controlling the humidity in the incubation room, and gas supply means (17) for supplying gas for controlling gas concentration in the incubation room, the adiabatic box main body comprising an outer box (21) made of a metal, an inner box (22) made of a metal, a heat insulating material (24) arranged inside the outer box between the outer and inner boxes, and an air layer (25) arranged more inside than the heat insulating material, and the incubator further comprises a support (18) for immersing the gas outlet port (17A) of the gas supply means (17) in the humidification water (16) in the humidifying tray (15). Therefore, the gas outlet port (17A) is supported by the support (18) so as to be immersed in the humidification water (16) in the humidifying tray (15) so that the gases jetted from the gas outlet port (17A) absorb the moisture to be humidified, while naturally raising in the humidification water (16), thereby enabling the humidified gases to be guided into the incubation room (4) by the circulation blower (14) and the duct (11) to improve the humidification faculty in addition to the supply of humidified gases.

DETAILED DESCRIPTION OF THE PREFERRED EMBODIMENTS

Embodiments of the present invention will be described in detail with reference to the accompanying drawings hereinafter.

(Embodiment 1)

Figure 1:
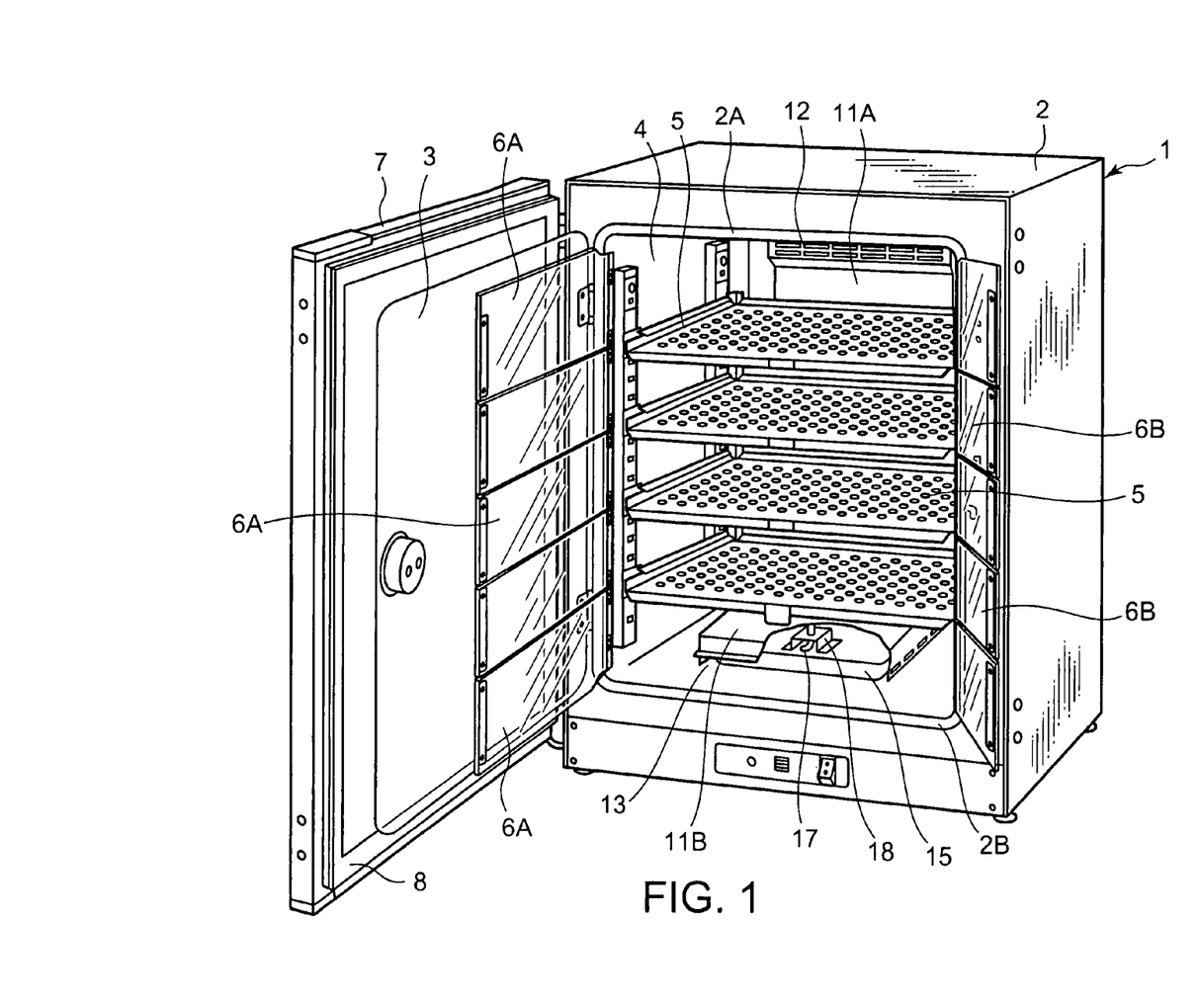
FIG. 1 is a perspective view of the incubator with its adiabatic door opened according to the present invention.
Figure 2:
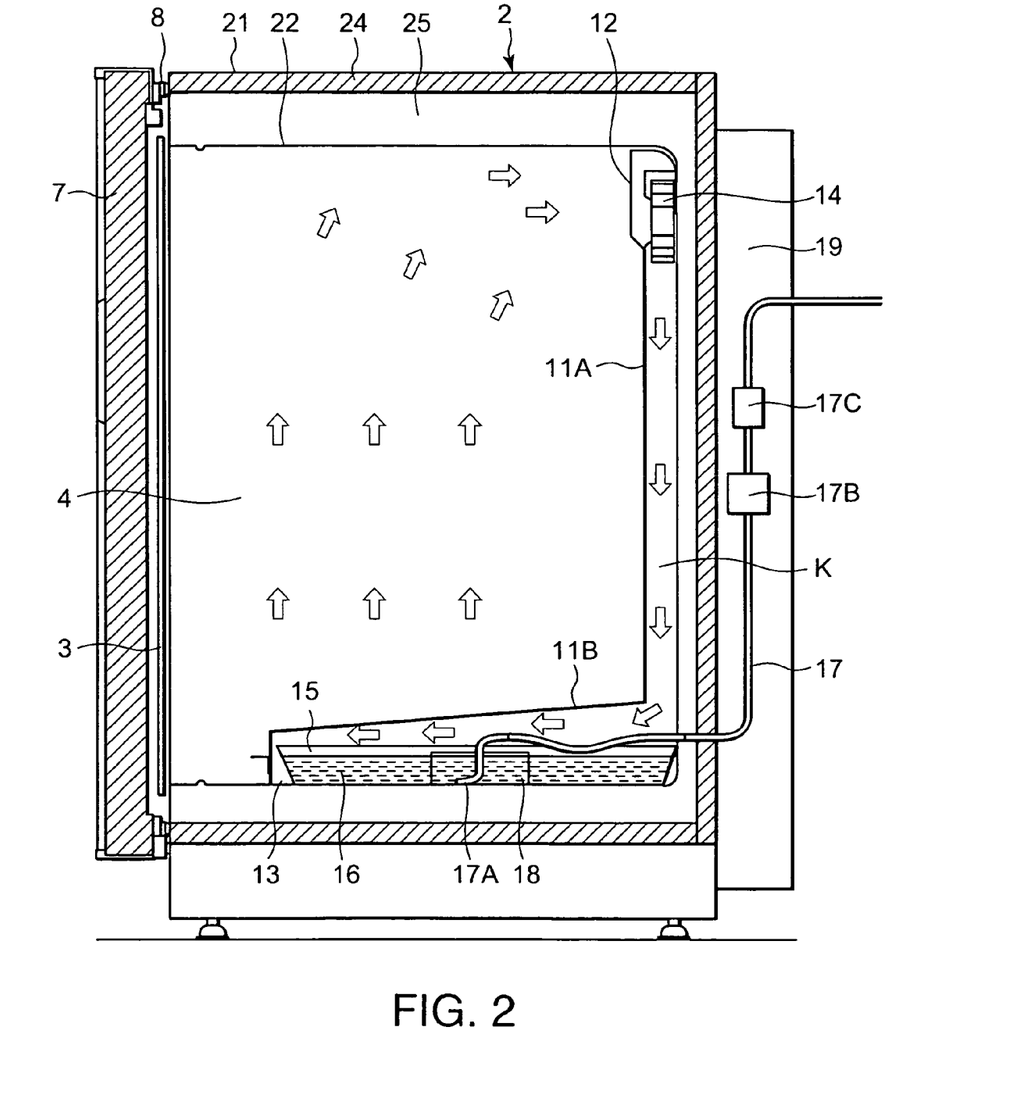
FIG. 2 is a sectional view of the incubator according to the present invention viewed from the right for explaining the air circulation mainly through the incubation room and the duct.
Figure 3:
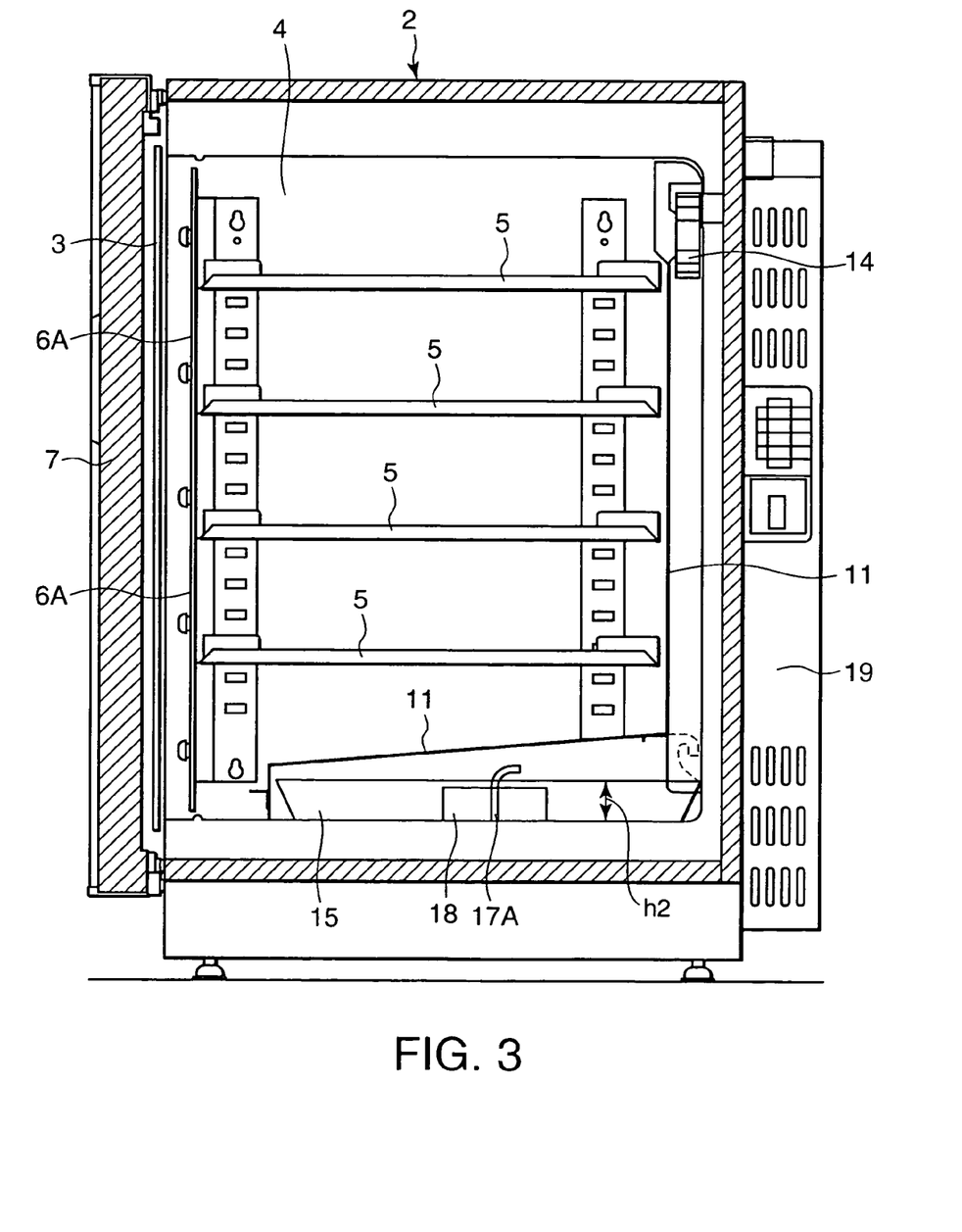
FIG. 3 is a sectional view of the incubator according to the present invention viewed from the right mainly illustrating the incubation room and the humidifying tray.

A multigas incubator 1 as an incubator of the first embodiment of the present invention comprises left hand opening doors (an outer and an inner door in more detail) and smaller doors as biparting doors as shown in FIGS. 1 to 3. An incubation room 4 is formed by a space surrounded by an adiabatic box main body 2 having an opening 2A in its front and a transparent door 3 as the inner door closing the opening 2A in an openable and closable manner. The transparent door 3 is supported at its left end by the adiabatic box main body 2 by means of hinges in an openable and closable manner so that when closed, the opening 2A is air-tightly closed with a gasket 2B provided at the opening of the incubation room 4. The adiabatic box main body 2 is provided with the seal member or gasket 2B along the periphery of the opening 2A of the adiabatic box main body 2 to seal the transparent inner door 3 and the main body 2.

The inside of the incubation room 4 is divided into upper and lower portions by a plurality of shelves 5 (into five portions by four shelves 5 in the illustrated embodiment). As the incubator 1 in the embodiment is a multigas incubator, the concentration of $O_2$ is frequently set and kept at a value of the order of 5%. In this case, the concentration of $O_2$ may be controlled by supplying an amount of dried $N_2$ gas into the incubation room after the doors are closed. For this purpose, in order to prevent the ambient air from entering the entire incubation room 4 divided in the plurality of portions, even if the inner door 3 is opened, the smaller doors 6A and 6B as the biparting doors inside the inner door 3 are divided into a plurality (five pairs in the illustrated embodiment) of parts correspondingly to the number of the portions of the incubation room 4 divided by the shelves 5. Reference numeral 7 denotes the adiabatic door as the outer door supported on the adiabatic box main body 2 through hinges in an openable and closable manner for preventing the heat from entering through the opening 2A of the incubation room. The adiabatic door 7 is provided on its inner periphery with a gasket 8 having magnets therein.

Arranged in the incubation room 4 is a duct 11 consisting of a rear face duct 11A and a bottom face duct 11B respectively spaced from the rear wall and the bottom wall of the adiabatic box main body 2 to form the air passage K, respectively. The rear face duct 11A is formed in its upper portion with suction openings 12 from which the air in the incubation room 4 is sucked into the duct 11 and exhausted through exhaust openings 13 provided in the bottom face duct 11B at its front end and side faces to forcedly circulate the air, in the incubation room 4. A circulation blower 14 for the forced circulation of the air in the incubation room is arranged in the duct 11 (in the upper portion of the duct 11 in the illustrated embodiment). The blower 14 comprises a fan, a motor and a shaft. The motor is located in a machine house 19 on the outer rear face of the incubation room 4 described later, while the shaft extends from the motor in the machine house 19 through the rear face of the main body 2 into the air passage K and is connected to the fan.

A humidifying tray 15 for storing water for humidification (that is, humidification water) 16 is arranged at the bottom of the incubation room 4 and in the duct 11. The humidification water 16 in the humidifying tray 15 is heated to be evaporated by heating means (not shown) arranged outside the bottom surface of an inner box 22 made of a metal, for example, stainless steel. By arranging the humidifying tray 15 in the duct 11 and at the bottom of the incubation room 4, it becomes possible to blow the humidified gas with high efficiency into the air passage K formed by the circulation blower 14 and the duct 11 and leading to the incubation room 4.

On the rear face of an outer box 21 of the adiabatic box main body 2 is formed a machine house 19 for arranging a motor for driving the circulation blower 14, gas supply means 17 for supplying gases such as $N_2$, $O_2$ and the like to the incubation room 4, and electrical equipment such as a control panel and the like (not shown).

Figure 4:
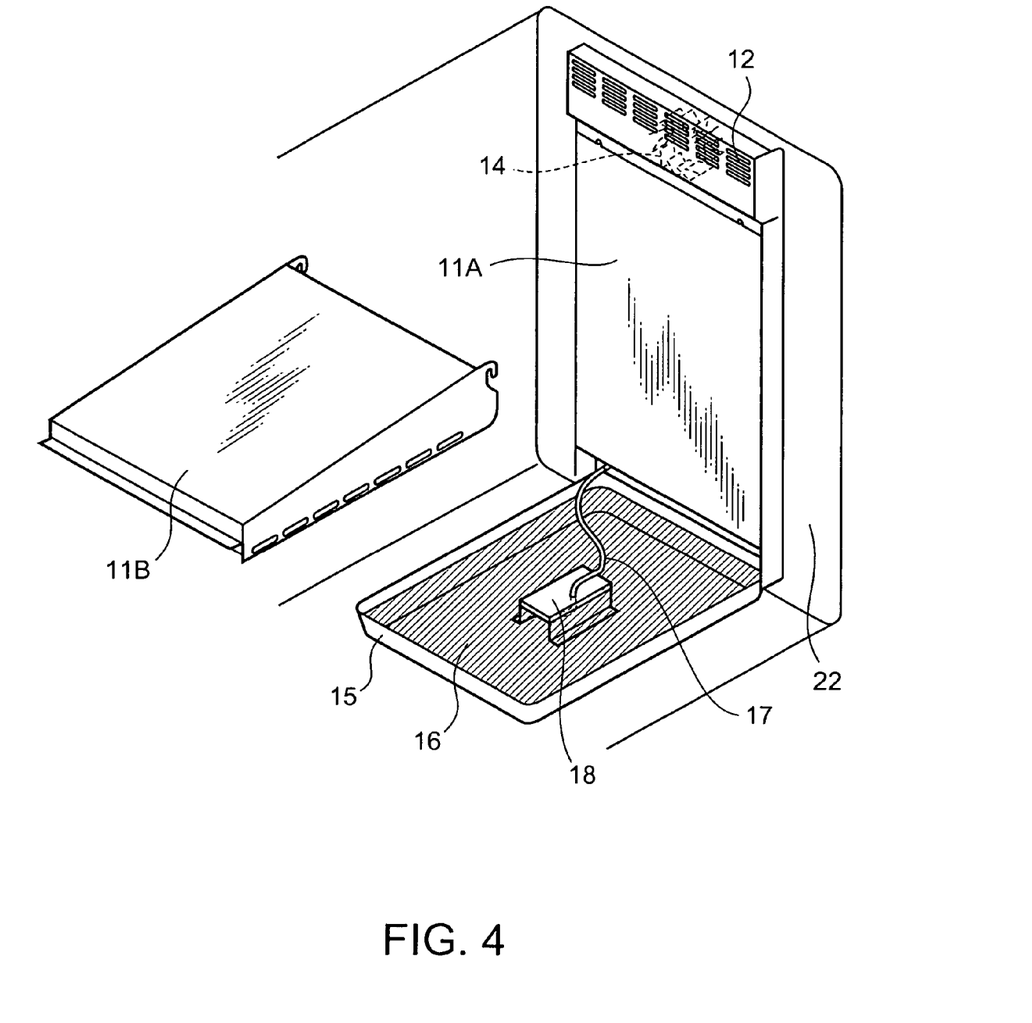
FIG. 4 is a perspective view of the incubation room to illustrate the humidifying tray and the support according to the present invention.
Figure 5:
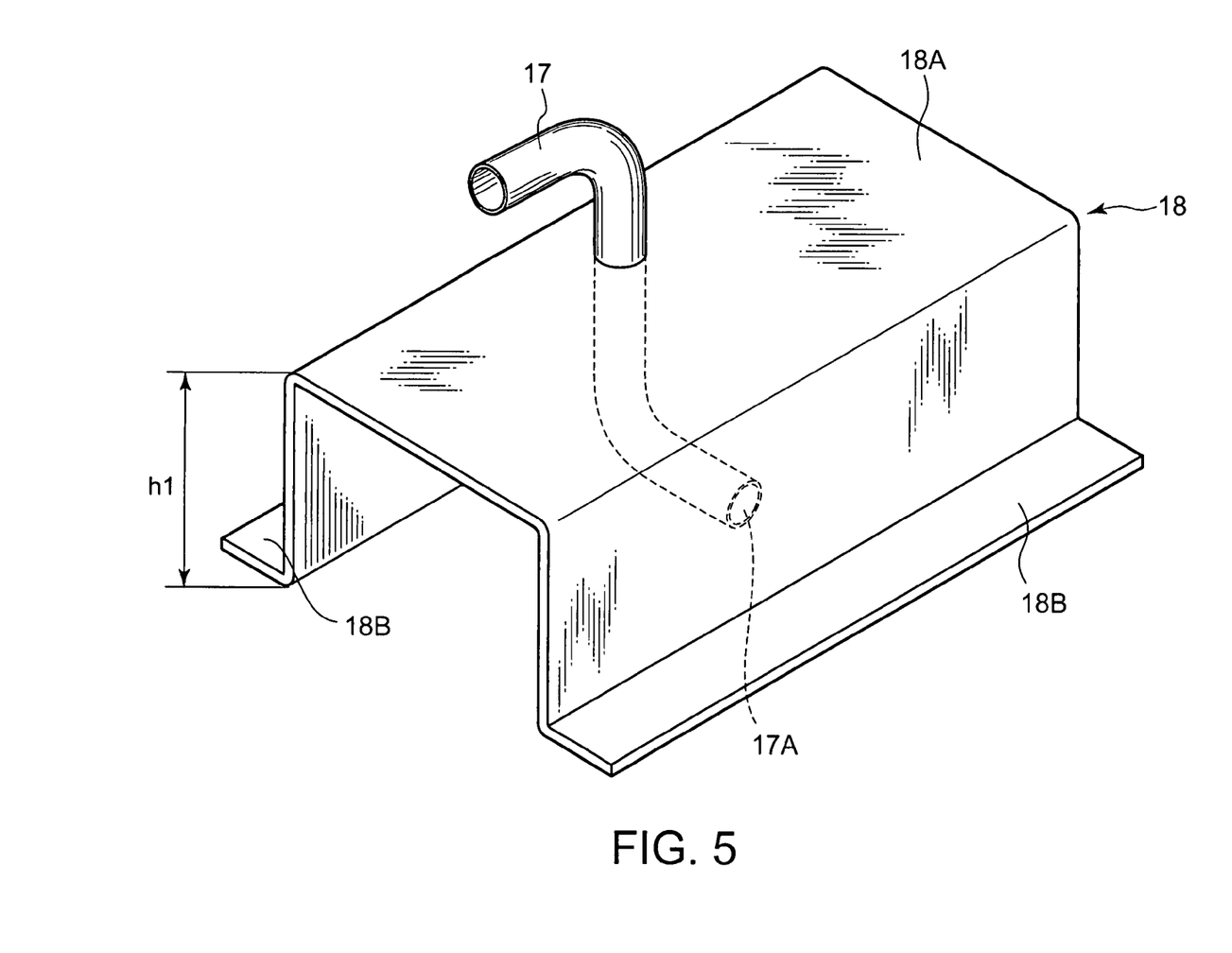
FIG. 5 is a perspective view illustrating the support in detail according to the present invention.

The gas supply means 17 comprises a gas supply tube 17A, an opening and closing valve 17B, a filter 17C and the like. The leading end portion of the gas supply tube 17A is supported by a support 18 such that the leading end portion is in the humidification water 16 in the humidifying tray 15. The support 18 consists of a main body 18A having a left and a right side face and an upper face to from a U-shape in cross-section and legs 18B for installing the main body 18A. The upper surface of the main body 18A provides restraining means for restraining the rising of the gas.

By providing the support 18 for supporting the gas outlet port 17A of the gas supply means 17, the gas outlet port 17A of the gas supply means can be supported to be immersed in the humidification water 16 in the humidifying tray 15. As the support 18 includes the restraining means 18A for restraining the rising of the gas, moreover, when the height h1 of the support 18 is set to a value substantially equal to the height h2 of the humidifying tray 15, it is possible to form a space between the restraining means 18A and the water surface of the humidification water. The evaporation of the humidification water will be promoted by the gas accumulated in the space, thereby improving the evaporation faculty. In order to observe the improvement of the evaporation faculty and the promotion of the evaporation, the times required for returning to a targeted humidity after the smaller doors are opened for a constant period of time were measured with the cases that the gas outlet port 17A of the gas supply means 17 is immersed in the humidification water 16 according to the present invention and that the gas is blown into the incubation room 4 or the air passage K in the conventional manner. The former according to the present invention required 12 minutes, while the later in the conventional manner took 36 minutes. It is apparent, therefore, that the evaporation faculty is improved by immersing the gas outlet port in the humidification water 16 according to the present invention.

As described above, the outlet port 17A of the gas supply means for supplying the gases for controlling the concentration of the gases in the incubation room 4 is immersed in the humidification water 16 in the humidifying tray 15, which is stored therein for the purpose of controlling the humidity in the incubation room 4 according to the invention. Accordingly, the gases (O$_2$ and N$_2$) supplied through the gas outlet port 17A can be jetted into the humidification water 16 in the humidifying tray so that the supply gases can be humidified and circulated in the incubation room 4.

Referring to FIGS. 2 and 3, the adiabatic box main body 2 comprises the outer box 21 made of a metal, the inner box 22 made of stainless steel, a heat insulating material 24 arranged on the inner side of the outer box 21 between the outer box 21 and the inner box 22, and an air layer (a so-called air jacket) 25 arranged more inside than the heat insulating material 24. Heaters (not shown) for heating the incubation room are arranged on both the left and right side faces, the upper face and the rear face of the inner box 22 forming the incubation room 4.

By providing the support 18 for supporting gas outlet port 17A of the gas supply means 17 to be immersed in the humidification water 16 in the humidifying tray 15 in the first embodiment, the gas outlet port 17A is supported to be immersed in the humidification water 16 in the humidifying tray 15 so that the gases jetted from the gas outlet port 17A absorb the moisture to be humidified, while rising naturally in the humidification water 16. Accordingly, the humidified gases can be guided into the incubation room 4 by means of the circulation blower 14 and the duct 11 so that in addition to the supply of the humidified gases the humidification faculty can be improved, thereby enabling shortening of the returning time to the targeted humidity after closing of the inner door (smaller door 6A or 6B in the embodiment).

Embodiment 2

The second embodiment of the present invention will be explained with reference to FIGS. 3 to 5 hereinafter. A support 18 in the second embodiment of the present invention is so arranged that opposite open ends of the support 18 are arranged in a line in the same direction as the air flowing direction in the air passage K formed by the bottom face duct 11B.

According to the support 18 in the second embodiment, it forms a passage in the same direction as the air flowing direction formed by the duct 11 so that the humidified gases are conducted with high efficiency in the air flowing direction formed by the circulation blower 14 and the duct 11 leading to the incubation room 4. Accordingly, the spacing between the support 18 and the water surface can be less than the spacing between the water surface and the duct 11 so that the air flow velocity in the space formed by the support 18 and the water surface becomes faster than the air flow velocity in the air passage K, with the result that the evaporation faculty of the humidification water can be improved by the increase in the air flow velocity.

FIG. 5 shows that the gas outlet port 17A is set transversely to a length of the U-shape of the support 18.

What is claimed is:

1. An incubator comprising:
an adiabatic box main body having an opening on a front face thereof, an adiabatic door mounted on the adiabatic box main body in an openable and closable manner, an inner door for openably closing the opening, an incubation room surrounded by the inner door and the adiabatic box main body for incubating samples such as cells, microbes and the like;
a gas supply to control gas concentration in the incubation room;
a humidifying tray for storing humidification water for controlling the humidity in the incubation room;
a gas outlet port of the gas supply means being immersed in the humidification water in the humidifying tray, from which gas from the gas supply is jetted into the humidification water;
a support for supporting the gas outlet port of the gas supply means; and
a duct and a circulation blower for causing forced convection of air in the incubation room;
wherein each one of the humidifying tray, the gas outlet port, the duct, and the circulation blower is contained inside the incubation room,
wherein the humidifying tray is arranged in the duct and at the bottom of the incubation room, and
wherein the support forms a passage in the same direction as the air flowing direction formed by the duct.

2. An incubator comprising:
an adiabatic box main body having an opening on a front face thereof, an adiabatic door mounted on the adiabatic box main body in an openable and closable manner, an inner door for openably closing the opening, an incubation room surrounded by the inner door and the adiabatic box main body for incubating samples such as cells, microbes and the like;
a gas supply to control gas concentration in the incubation room;
a humidifying tray for storing humidification water for controlling the humidity in the incubation room;
a gas outlet port of the gas supply means being immersed in the humidification water in the humidifying tray, from which gas from the as supply is jetted into the humidification water; and
a duct and a circulation blower for causing forced convection of air in the incubation room;
wherein each one of the humidifying tray, the gas outlet port, the duct, and the circulation blower is contained inside the incubation room,
wherein the humidifying tray is arranged in the duct and at the bottom of the incubation room;
wherein the support comprises an inverted U-shape including side faces and an upper surface that forms a passage and restrains rising of the gas,
wherein a height of the support is set to a value substantially equal to a height of the humidifying tray, whereby a space is formed between the upper surface and a water surface of the humidification water, and
wherein opposite ends of the U-shape are arranged in a line in a same direction as an air flowing direction in the duct.

3. An incubator comprising:
an adiabatic box main body having an opening on a front face thereof, an adiabatic door mounted on the adiabatic box main body in an openable and closable manner, an inner door for openably closing the opening, an incubation room surrounded by the inner door and the adiabatic box main body for incubating samples such as cells, microbes and the like;
a gas supply to control gas concentration in the incubation room;
a humidifying tray for storing humidification water for controlling the humidity in the incubation room;
a gas outlet port of the gas supply means being immersed in the humidification water in the humidifying tray, from which gas from the gas supply is jetted into the humidification water; and
a duct and a circulation blower for causing forced convection of air in the incubation room;

wherein each one of the humidifying tray, the gas outlet port, the duct and the circulation blower is contained inside the incubation room, wherein the humidifying tray is arranged in the duct and at the bottom of the incubation room;

wherein the support comprises an inverted U-shape including side faces and an upper surface that forms a passage and restrains rising of the gas, wherein a spacing between the support and a water surface of the humidification water is less than a spacing between the water surface of the humidification water and the duct, and wherein opposite ends of the U-shape are arranged in a line in a same direction as an air flowing direction in the duct.

* * * * *